United States Patent [19]

Spielberg

[11] Patent Number: 4,925,555
[45] Date of Patent: May 15, 1990

[54] ULTRAFILTERING HYBRID ARTIFICIAL ORGAN

[76] Inventor: Theodore E. Spielberg, 10 Pinewood Cir., Wellesley, Mass. 02181

[21] Appl. No.: 193,156

[22] Filed: May 5, 1988

Related U.S. Application Data

[63] Continuation of Ser. No. 759,970, Jul. 29, 1985, abandoned, which is a continuation of Ser. No. 507,997, Jun. 27, 1983, abandoned, which is a continuation of Ser. No. 321,099, Nov. 13, 1981, abandoned.

[51] Int. Cl.$^5$ .............................................. B01D 63/06
[52] U.S. Cl. .................................. 210/137; 210/259; 210/295; 210/321.83
[58] Field of Search ............... 210/638, 641, 650, 651, 210/257.2, 259, 261, 295, 321.83, 434, 137

[56] References Cited

U.S. PATENT DOCUMENTS

| | | | |
|---|---|---|---|
| 3,734,851 | 5/1973 | Matsumura | 210/641 X |
| 3,827,565 | 8/1974 | Matsumura | 210/641 X |
| 4,013,564 | 3/1977 | Nose | 210/434 |
| 4,024,059 | 5/1977 | Sausse | 210/195 |

OTHER PUBLICATIONS

Reach, G. et al., "Functional Evaluation of a Bioartificial Pancreas ..." *Diabetes*, vol. 30, 4/1981, p. 296–301.

*Primary Examiner*—Frank Spear
*Attorney, Agent, or Firm*—Martin J. O'Donnell

[57] ABSTRACT

An artifical hybrid organ or gland is formed from two serially-interconnected chambers, the first of which comprises an ultrafiltration chamber which forms an ultrafiltrate from the blood stream applied to it and the second of which comprises a cell exchange chamber which, though immunologically isolated by microporous membranes, receives both the bloodstream and the ultrafiltrate and which rapidly exchanges selected constituents with both before they recombine in order to provide a corrected physiological response to constituents in the blood. Additionally, an optional excretory duct may be employed to channel a portion of the treated ultrafiltrate away from the bloodstream.

11 Claims, 3 Drawing Sheets

ULTRAFILTERING HYBRID ARTIFICIAL ORGAN

This is a continuation of application Ser. No. 759,970, filed on Jul. 29, 1985, which is a continuation of Ser. No. 507,997, filed Jun. 27, 1983, which is a continuation of Ser. No. 321,099, filed Nov. 13, 1981, all now abandoned.

BACKGROUND OF THE INVENTION

A. Field of the Invention

The invention relates to artificial organs and glands and comprises an ultra filtering hybrid artificial organ or gland for providing a corrected physiological response to blood constituents in a rapid manner.

B. Prior Art

Increased activity in recent years has been devoted to developing artificial organs of various kinds. Much of the early effort has been devoted to developing organs which perform primarily mechanical functions, e.g., the heart. More recent activity has extended to the construction of organs which attempt to duplicate body physiology, e.g., dialysis devices and the like. This typically presents a more difficult problem than duplication of mechanical functions, due to the compexities of the physiologic system. An even greater level of difficulty is presented in the design and construction of devices which duplicate glandular functions, and progress in this area has been less rapid than in others.

Several devices which perform the function of the endocrine pancreas have been proposed. Aside from wholly artificial devices that depend on glucose sensors, algorithmic contollers, and refillable insulin reservoirs, attempts have been made to utilize natural pancreatic beta cells within an artificial structure as a form of protected and facilitated transplantation known as a hybrid artificial pancreas. Such devices include mechanisms for closely contacting the blood of a patient with this living glandular material, usually through a microporous membrane separating the two, so that the glandular material may respond to various constituents in the blood and exchange selected material therewith by simple diffusion, yet avoid rejection by host lymphocytes and antibodies that are too large to pass through the pores. In these devices, the glandular material actually adheres to the membranes and grows into and encroaches the pores resulting in proximity to the blood compartment improving diffusion back and forth across the membrane.

Such devices constitute an advance in the art but suffer the critical disadvantage, among others, that there is a significant time delay in the process of diffusion of various constituents, such as glucose and insulin, across the membrane despite the use of large membrane surface areas. This delay is undesirable to the extent that it departs from the normal tight physiological control and, in some cases, may present a risk to an individual dependent on such a device for rapid response to abnormal body conditions, i.e., a stressed diabetic relying on the device for production of insulin in response to acutely changing glucose levels in the blood. Additionally, this loose control of blood sugar may prevent the long-term tight control of diabetes necessary to prevent the complications of retinopathy and nephropathy, neuropathy, and accelerated vascular disease that all too often results in blindness, kidney failure, impotence, and premature heart attack.

SUMMARY OF THE INVENTION

A. Objects of the Invention

Accordingly, it is an object of the invention to provide an improved hybrid artificial organ or gland.

Further, it is an object of the invention to provide an improved hybrid artificial gland.

Specifically, it is an object of the invention to provide a hybrid artificial pancreas, liver, or kidney, providing an improved response to body stimuli.

B. Brief Description of the Invention

For purposes of illustration, the present invention will be described primarily in terms of an artificial gland and, more specifically, a hybrid artificial pancreas. However, it should be understood that the device of the present invention is also particularly well adapted to function as an artificial non-glandular organ as well (e.g., liver and kidney), with certain modifications that will be described later, as well as an endocrine gland in general. In accordance with the preferred embodiment of the present invention, I provide an ultra filtering hybrid artificial pancreas formed from two treatment stations in series, the first of which forms an ultrafiltrate through a microporous membrane from preferably arterial blood supplied to it, and the second of which contains a cellular exchange medium, such as beta cells, which respond to both the ultrafiltrate and to the whole blood for necessary oxygenation, to provide the desired physiologic response to constituents in the ultrafiltrate and in the blood. The ultrafiltrate and the blood, now carrying the response constituent(s) of the cellular exchange medium (insulin), are then recombined, either by direct mixing or by reabsorption of the ultrafiltrate into the bloodstream via a microporous membrane, and the blood returned to the body system.

Ultrafiltration (as contrasted with simple diffusion) relies on a hydrostatic pressure gradient across a membrane (instead of a concentration gradient); this results in large numbers of molecules "streaming" unidirectionally through pores in unison (rather than moving bidirectionally as in simple diffusion). This phenomenon of ultrafiltration is referred to technically as "convective mass transfer" or "solute drag", since adjacent molecules drag each other across the membrane; in consequence, molecules such as glucose for example, are washed across the ultrafiltration membrane much more rapidly than would be the case with simple diffusion. Consequently the surface area of the ultrafiltering membranes may be significantly reduced as compared to diffusion membranes in previous devices, thereby allowing more favorable design alternatives.

The resulting component of ultrafiltrate is generally quite similar to that of the fluid compartment of whole blood from which it is derived except for a depressed calcium level, and the absence of proteins and cells. Specifically, the concentration of glucose in the ultrafiltrate closely tracks the level of glucose in the blood from which it is derived at any given time. Thus, the response of beta cells to the ultrafiltrate is very close to the normal physiological response of these cells in a nondiabetic individual. Moreover, the glucose-insulin exchange across a semipermeable membrane with beta cells on one side and ultrafiltrate on the other is significantly faster than that across a corresponding membrane having beta cells on one side and whole blood on the other side, where proteins and blood cells interfere with transfer through the membrane pores. Thus, the device of the present invention provides a significantly faster physiological response than one in which the exchange takes place by simple diffusion with whole blood only. However, it also provides immunologically protected contact, through a microporous semipermeable membrane, between the beta cells and whole blood which contains oxygenated red blood cells in order to maintain the continued viability of the beta cells.

In the preferred embodiment of the invention, the exchange station comprises a chamber having first and second tubular membrane coils formed therein for transporting ultrafiltrate and blood, respectively, through the device. The chamber is filled with glandular or organ materials such as beta cells which, in response to glucose or other constituents in the ultrafiltrate and/or in the blood, release insulin which crosses the respective membranes to the ultrafiltrate and to the blood. The ultrafiltrate and the blood are then recombined, after their exposure to the beta cells, for subsequent utilization by the body. In this embodiment, the membrane separating the ultrafiltrate from the exchange cells may advantageously have a significantly larger pore size than that separating the blood stream from the cells, since the ultrafiltrate is free of adverse immunological agents such as cells and antibodies which might otherwise attack the exchange cells. A larger pore size provides more rapid transfer of insulin to the ultrafiltrate and thus, ultimately, to the patient's bloodstream.

In another embodiment of the invention, the ultrafiltrate is supplied directly to the exchange chamber where it comes in direct contact with the beta cells for ultrarapid stimulation of insulin production. The ultrafiltrate is then re-absorbed through the pores of the membrane separating the bloodstream from the exchange medium and it is then returned to the body together with the blood. In cases where the reabsorption rate of this system would be inadequate, due to the particular flow rates or membranes used, or due to other such factors, provision may be made for directly draining a portion of the insulin-containing ultrafiltrate from the cellular exchange portion by a mechanical bypass which reunites it with the bloodstream. This alternative results in yet another unique feature of the device, that of transporting insulin directly to the bloodstream, instead of relying on the much slower diffusion of insulin across microporous membranes as in previous devices. This results in a shorter, more nearly "correct" physiological response time, and compensates for the slower diffusion rate of insulin compared to glucose, since the diffusion rate is a function of molecular weight rather than solute size as in ultrafiltration. A microporous membrane of much greater pore size than that of the membrane carrying the blood through the exchange channel may be interposed in the drain to prevent loss of cells from the exchange chamber while allowing rapid passage of insulin with the ultrafiltrate. Due to the tendency of beta cells to aggregate and clump on membrane walls, and thus anchor themselves to it, it is possible that even the drain membrane may be dispensed with, with only slight loss of beta cells.

The ratio of ultrafiltrate flow to blood flow directly affects the response characteristics of the device. The greater the ultrafiltrate flow in relation to the blood flow, the more rapidly the device responds to physiologic changes in the bloodstream. However, when the device is used as a hybrid organ, where a portion of the ultrafiltrate may result in an excretory product (e.g., bile or urine), too great a ratio of ultrafiltrate flow to blood flow could result in adverse physiological effects (e.g. dehydration). This ratio may be controlled by varying the hydrostatic pressure in the ultrafiltration portion, as well as by appropriate selection of the ultrafiltration membrane area and configuration, the diffusion membrane area and configuration, membrane thickness, pore size, transfer coefficients, and support design, especially the size and configuration of the transport tubes for the blood and the ultrafiltrate. Additionally, this ratio can be controlled by bypassing portions of the blood flow around the ultrafiltration station or around the cellular exchange portion, or by bypassing portions of the ultrafiltrate flow around the cellular exchange station. Various embodiments effectuating these flow patterns are described herein.

When used as a hybrid artificial organ, a channel may be formed to drain a portion of the treated ultrafiltrate away from the bloodstream, to thereby remove, for example, waste products such as urine or bile when the device is utilized as an artificial kidney or liver.

DETAILED DESCRIPTION OF THE INVENTION

The foregoing and other and further objects, features, and advantages of the present invention will be understood more readily on reference to the following detailed description of the invention, when take in conjunction with the accompanying drawings in which.

Figure 3A:
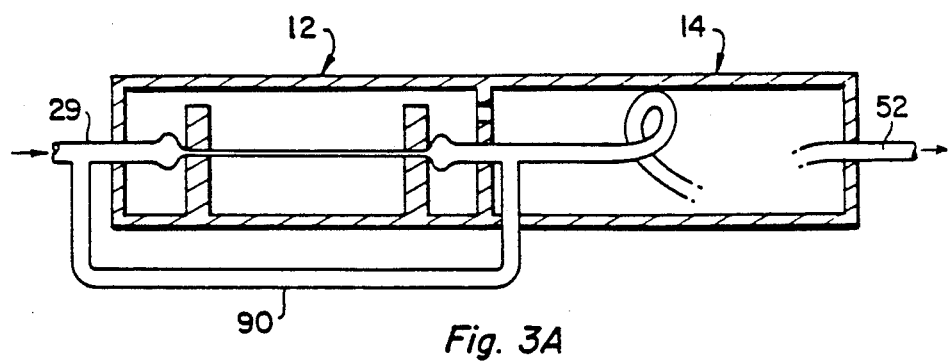
Figure 3B:
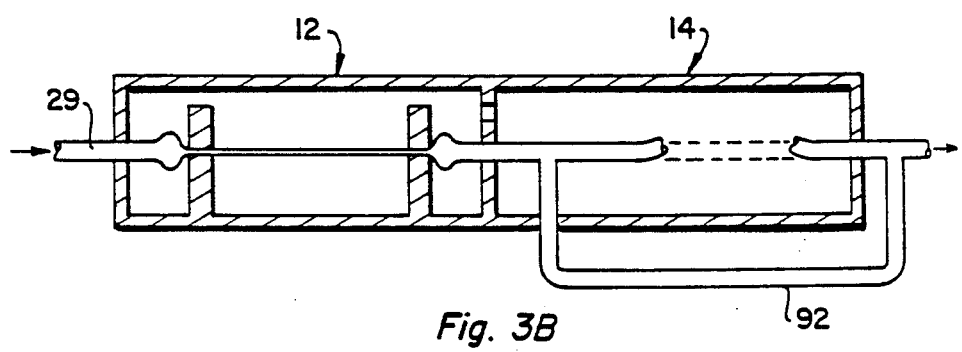
Figure 3C:
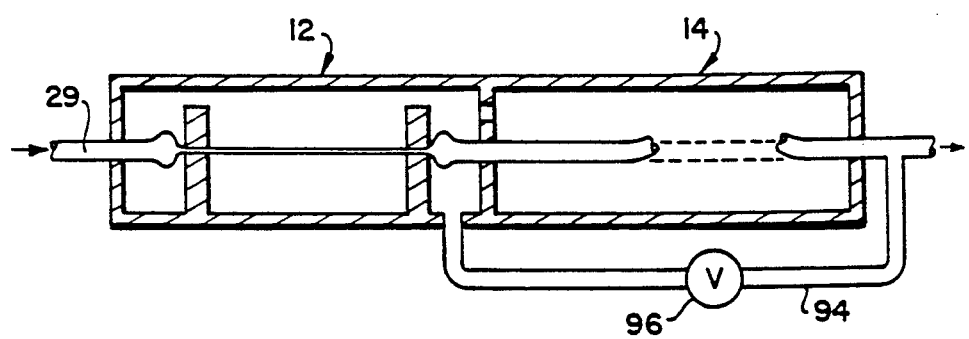
Figure 4:
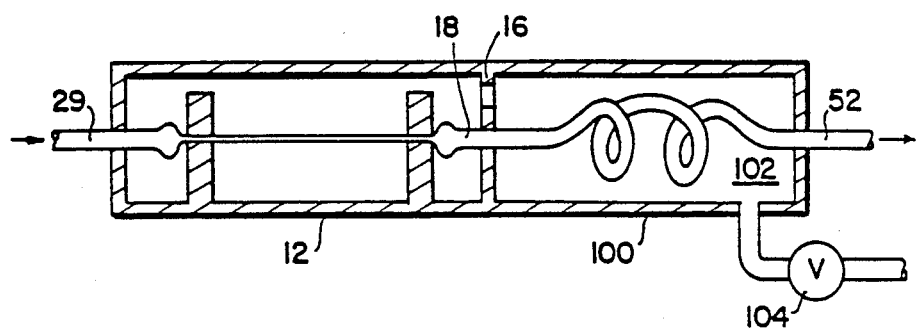

FIGS. 3A, 3B, and 3C are diagrammatic illustrations of still further alternative embodiments of the invention showing additional techniques for controlling the ratio of ultrafiltrate flow to whole blood flow; and FIG. 4 is a diagrammatic illustration of an artificial organ in accordance with my invention.

Figure 1:
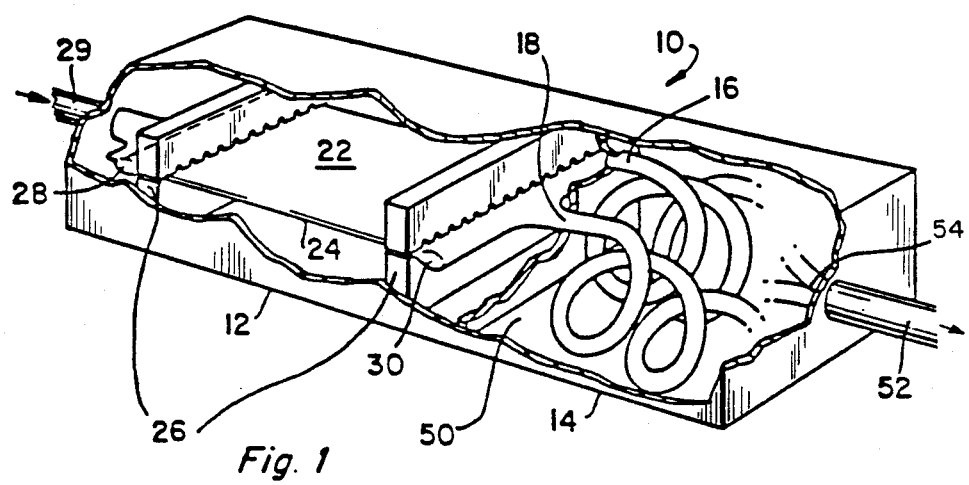
FIG. 1 is a view in perspective, with portions cut away, of a preferred embodiment of the invention showing the serially-connected ultrafiltration and cellular chambers.

In FIG. 1, an artificial gland 10 in accordance with the invention is formed from an ultrafiltration chamber 12 serially connected to a cellular exchange chamber 14 by means of tubular flow paths 16, 18. The ultrafiltration chamber may take any of a number of forms commonly used in the medical field. For purposes of illustration, the chamber is shown as comprising a generally rectangular enclosure 20 having upper and lower membranes 22 and 24, respectively, closely spaced apart from each other and supported by clamping structures 26 at opposite ends. The membranes open outwardly at their ends into manifolds 28, 30, respectively. A tubular cannula 29, which is preferably connected to the artery of a human or animcal body, receives blood from the body and carries it to the manifold 28. After passage through the narrow channel between the membranes 22, 24, the blood accumulates in manifold 30 and thereafter passes into the cellular exchange chamber 14 via conduit 18.

During its passage between the membranes, liquid constituents of the blood are forced outwardly through the one or both of the membranes to form an ultrafiltrate which collects within the interior of chamber 21. The ultrafiltrate is then drawn off into chamber 14 via conduit 16. Effectively, the reduced cross-sectional flow area between the membranes provides the requisite back pressure to support ultrafiltration action, while the source of blood provides the requisite positive pressure to do so.

Tubular conduits 16 and 18 continue as separate conduits within cellular exchange chamber 14 for separate exposure to exchange media 50 within the chamber. For purposes of illustration, chamber 14 is shown as a generally rectangular hollow chamber. The conduits themselves are formed from microporous semipermeable membranes whose pore size and wall thickness are such as to allow the transport of selected products across them, while effectively containing the fluid streams within them. For purposes of providing an artificial pancreas, the media 50 comprises pancreatic beta cells which provide a source of insulin in response to appropriate physiologic signals from the ultrafiltrate and the blood, respectively. Glucose and oxygen contained within the ultrafiltrate within conduit 16 permeate through the membraneous pores of this conduit into the medium 50 within the chamber 14, while insulin permeates through the pores in the reverse direction from the cellular medium 50 into the interior of the conduit 16 where it mixes with the insulin-containing ultrafiltrate within this conduit and is carried off with it. In like fashion, glucose and insulin are exchanged across the membraneous pores of conduit 18 between the blood within the conduit and the cellular exchange medium exterior to the conduit. Importantly, oxygen and other nutrients are transported across the pores of conduit 18 into the cellular medium 50 in order to sustain the beta cells. The conduits 16 and 18 are rejoined into a single conduit 52 at a transition junction 54. Conduit 52 returns the treated blood to the body, such as by connection into a vein.

The operation of the device of FIG. 1 is as follows: Arterial blood diverted from the body to be treated flows through tubular conduit 29 into ultrafiltration chamber 12 where it is separated into an ultrafiltrate component of essentially similar composition to the blood fluid, but lacking in proteins and blood cells, and a blood component containing these constituents. The ultrafiltration portion preferably provides a constricted path for the blood flowing into it in order to build up a suitable pressure to efficiently perform the ultrafiltration. It is expected that in most cases the human or animal body will provide sufficient pressure to support the requisite ultrafiltration portion pressure while continuing fluid blood flow through the device. Where this is not the case, it may be necessary to supplement the body-generated pressure by means of an auxilliary pumping device creating either a positive pressure on the inlet side (i.e., the side adjacent conduit 29) or creating a negative pressure on the outlet side (i.e., the side adjacent conduit 52). In either event, the resultant ultrafiltrate and whole blood component are passed along to the cell exchange chamber 14 via conduits 16 and 18, respectively, where they receive insulin through the tubular membraneous wall from the medium 50. On recombining in conduit 52, the insulin-containing ultrafiltrate and blood carry this insulin back to the body for utilization by it in controlling the glucose levels within the blood.

Figure 2:
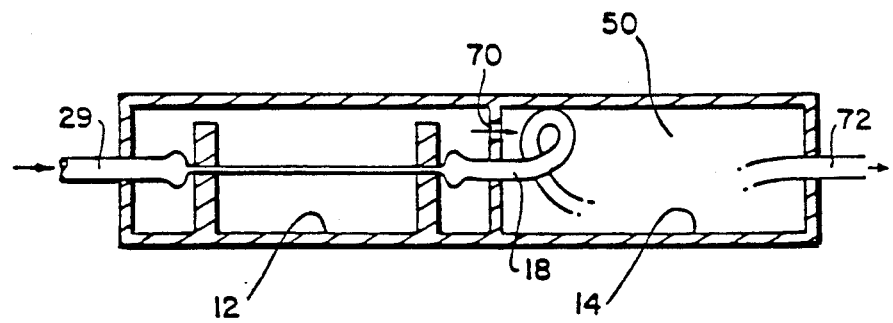
FIG. 2 is a diagrammatic view of an alternative form of the invention in which the ultrafitrate is brought into direct contact with the beta cells.
Figure 2A:
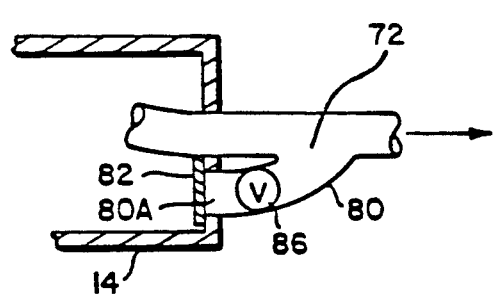
FIG. 2A is a diagrammatic view of an alternative form of the invention illustrated in FIG. 2 showing the provision of an auxiliary shunt for expedited recombination of the treated ultrafiltrate and the whole blood component.

Turning now to FIG. 2, a first alternative embodiment in accordance with the present invention has the ultrafiltration chamber 12 serially connected to a cellular exchange chamber 14 as in FIG. 1. A conduit 70 carries ultrafiltrate from the ultrafiltration chamber to the cell chamber, while a conduit 18 carries the remaining whole blood component from chamber 12 to chamber 14. However, in contrast to FIG. 1, the conduit 70 does not continue into the chamber 14 in the form of a tubular semipermeable membrane as in FIG. 1 but, instead, discharges its contents directly into the cellular portion 50 for direct contact with the cellular exchange material (i.e., beta cells) therein. Also, as in the embodiment of FIG. 1, an inlet conduit 29 carries blood from the body, preferably from a high pressure location thereof such as an artery, and a conduit 72 carries the treated blood back to the body, preferably to a low pressure location thereof such as a vein. Again, however, unlike the embodiment of FIG. 1, the conduit 72 is continuous only with the conduit 18, and not with the conduit 70 as well. Thus, there is no direct protection between conduit 70 and conduit 72, in contrast to the embodiment of FIG. 1. Instead, the ultrafiltrate material supplied to the interior of chamber 14 obtains access to the conduit 72 only through diffusion through the semipermeable membrane pores of conduit 18. This diffusion is aided by the osmotic pressure difference between the pressure of the insulin-containing ultrafiltrate in chamber 14 and the reduced pressure of the blood component in conduit 18; the latter is at a lower hydrostatic pressure while maintaining colloid osmotic pressure. This results in a net fluid and solute flow from the insulin containing ultrafiltrate into the blood conduit according to the well-known principles of the Starling equilibrium of capillary exchange.

In another embodiment, the cells in the cellular exchange portion are microencapsulated in a microporous material (membrane) which prevents them from growing into the pores of the other microporous membranes. In this embodiment ultrafiltrate and blood may (optionally) directly mix together in the cellular exchange chamber.

Where the ultrafiltrate return rate to conduit 72 in FIG. 2 is insufficient to reach equilibrium under steady-state conditions, the filtration rate of ultrafiltrate into the conduit 72 may be increased by further decreasing the pressure in conduit 70 by means of a pump connected to this conduit. Alternatively, a bypass conduit 80 may be connected between chamber 14 and conduit 72 to carry additional ultrafiltrate directly from the chamber into the conduit 48. A semipermeable membrane 82 mounted on spacer blocks 84 connected to the interior walls of chamber 14 provides for passage of the ultrafiltrate from this chamber into conduit 72. A valve 86 allows for ajustment of the ultrafiltrate flow rate so that, under steady-state conditions, the rate at which ultrafiltrate is removed in chamber 12 from the blood being treated is the same as the rate at which the ultrafiltrate is being retrained to the conduit 72. The area and configuration of the membrane 82 and, correspondingly, the volume of the inlet chamber 80A, may be adjusted as appropriate to vary the ultrafiltrate return rate to conduit 80, and thus to conduit 72.

Turning now to FIG. 3, various alternatives for establishing the desired ultrafiltration flow-to-blood flow ratio are shown. In FIG. 3A, a shunt 90 bypasses a portion of blood from conduit 29 prior to its entrance into the ultrafiltration chamber 12. Accordingly, the production of ultrafiltrate is diminished by this arrangement and the ratio of ultrafiltrate to blood is correspondingly diminished. In FIG. 3B, a portion of the blood component exiting from chamber 12 is bypassed around the cell exchange chamber by means of a shunt conduit 92. This arrangement leaves intact the ratio of ultrafiltrate to whole blood established by the geometry of chamber 12 and the inlet and outlet pressures and flow rates therein, but varies the amount of blood contacting the exchange cells in chamber 14. Accordingly, its effect is equivalent to that of the increase in the ultrafiltration flow-to-blood flow ratio, although it decreases the total amount of blood exposed to the exchange cells. Finally, in FIG. 3C, a portion of the ultrafiltrate is bypassed around chamber 14 through a conduit 94 containing a valve 96 for controlling the flow in conduit 94, and may be returned to the blood and/or partially drained via an optional excretory duct. This embodiment leaves intact the actual ratio of ultrafiltration flow-to-blood flow generated by the ultrafiltrate chamber 12, but decreases the effective ratio of ultrafiltration flow-to-blood flow since it diminishes the amount of ultrafiltrate exposed to exchange cells in chamber 14.

So far I have described the preferred and various alternative embodiments of an artificial gland in accordance with my invention. The invention may also be extended to artificial organs, such as livers and kidneys, among others. As seen in FIG. 4, an artificial liver, for example, comprises a filtration chamber 12 receiving blood to be treated via a conduit 29 and applying it, after it has been ultrafiltered, through conduit 18 to a cell exchange chamber 100. A conduit 16 carries the ultrafiltrate to chamber 100. Conduit 18 extends through chamber 100 in the form of a multiply-looped coil formed from a semipermeable membrane retaining protein and other major blood constituents on the inside thereof for flow through the chamber within the conduit and returned to the body or other source through conduit 52 as was previously the case. During passage through chamber 100, the ultrafiltered blood exchanges various constituents with liver cells 102 within the chamber. Specifically, oxygen, certain nutrients, and waste products flow from the blood to the liver cells 102 within the chamber. These blood products sustain the liver cells, and also stimulate them to produce bile. Excretory products are then returned, via a conduit 104, to the urinary bladder or other parts of the urinary tract in the case of the kidney, or to the intestine, in the case of the liver. Alternatively, the conduit may lead to a collection bag outside the body.

CONCLUSION

From the foregoing, it will be seen that I have provided an improved hybrid artificial organ and gland. The device of the present invention provides an effective substitute for injured or diseased organs or glands more nearly approximating the rapid response of an actual body to acutely changing physiological demand and is expected to be capable of sustained functioning over extended periods of time. Various embodiments provide adjustment of the effective ratio of ultrafiltration flow to blood flow to adjust to differing body demands and an optional excretory channel is provided when appropriate for some organ modes.

It should also be understood that the term "pores" is used in a functional sense, in that some membranes without microscopically visible pores are capable of transporting substances by physically solubalizing them within the membrane and delivering them across the membrane. It should be understood that different types of cells may be used together for beneficial effect, e.g., mast cells that produce heparin which prevents clotting may be added to beta cells in the cellular exchange portion. Additionally, the cells may be frozen, grown in culture media, pretreated with chemicals or blood constituents such as antilymphocytic globulin to further aide in immunological protection, or treated in other ways promote their survival and longevity or improve their functional response.

It is further understood that the membraneous portions of the device may be employed in various configurations including, but not limited to, flat plates, coils, capillary tubes (woven and unwoven), singly, in multiples, and in various preferred combinations.

Having illustrated and described my invention, I claim:

1. An ultrafiltering hybrid artificial organ or gland, comprising
   A. means forming an ultrafiltration chamber for receiving blood from a source and forming therefrom a first fraction comprising blood cells and proteins and a second fraction free of said blood cells and proteins,
   B. means forming a cellular exchange chamber separate from, and serially connected to, said ultrafiltration chamber for receiving said first and second fractions in the separated state and configured to contain a cellular exchange medium for separately contacting said first and second fractions for treatment thereof by exchanging selected constituents therewith, and
   c. means for recombing the treated fractions.

2. An ultrafiltering hybrid artificial organ or gland according to claim 1 in which said means forming a cellular exchange chamber includes a microporous membrane transfer means for transferring said constituents across said membrane for exchange with at least said blood fraction therethrough to form said treated blood fraction.

3. An ultrafiltering hybrid artificial organ or gland according to claim 2 which includes means for directly intermixing said treated ultrafiltrate and said treated blood fraction after their exposure to said cellular exchange medium.

4. An ultrafiltering hybrid artificial organ or gland according to claim 2 in which said cellular exchange chamber receives said ultrafiltrate for direct contact with said cellular exchange medium and includes means forming a first microporous membrane-enclosed channel for passage of said blood fraction therethrough and for exchange of constituents with both said exchange medium and said ultrafiltrate through said membrane.

5. An ultrafiltering hybrid artificial organ or gland according to claim 1 in which said means forming a cellular exchange chamber includes means forming a first microporous membrane-enclosed channel for passage of said blood fraction therethrough, and a second microporous membrane-enclosed channel for passage of ultrafiltrate therethrough, said channels being positioned for contact with said cellular exchange medium within said cellular exchange chamber.

6. An ultrafiltering hybrid artificial organ or gland according to claim 1 which includes flow means for altering the ratio of ultrafiltrate flow to blood fraction flow applied to said means forming a cellular exchange chamber.

7. An ultrafiltering hybrid artificial organ or gland according to claim 6 which comprises means for shunting a portion of the blood from said source around said means forming an ultrafiltration chamber prior to its application to said means forming a cellular exchange chamber.

8. An ultrafiltering hybrid artificial organ or gland according to claim 6 which comprises shunting a portion of the blood fraction from said ultrafiltration chamber around said means forming a cellular exchange chamber.

9. An ultrafiltering hybrid artificial organ or gland according to claim 6 which comprises means for shunting a portion of the ultrafiltrate around said means forming a cellular exchange chamber.

10. An ultrafiltrating hybrid artificial organ or gland according to claim 6 containing an excretory duct to drain a portion of the treated ultrafiltrate away from the blood stream.

11. An ultrafiltering hybrid artificial organ or gland according to claim 1 containing an excretory duct to drain a portion of the treated ultrafiltrate away from the blood stream.

* * * * *